(12) United States Patent
Williams et al.

(10) Patent No.: US 8,105,620 B2
(45) Date of Patent: Jan. 31, 2012

(54) BED BUG INSECTICIDE

(76) Inventors: Wesley L Williams, New Orleans, LA (US); William Monroe Stephenson, Slidell, LA (US)

( * ) Notice: Subject to any disclaimer, the term of this patent is extended or adjusted under 35 U.S.C. 154(b) by 21 days.

(21) Appl. No.: 12/565,653

(22) Filed: Sep. 23, 2009

(65) Prior Publication Data

US 2011/0070308 A1    Mar. 24, 2011

(51) Int. Cl.
*A61K 36/58* (2006.01)
*A61K 36/752* (2006.01)
*A61K 36/00* (2006.01)

(52) U.S. Cl. ........ 424/405; 424/725; 424/761; 424/736; 568/875

(58) Field of Classification Search .................. None
See application file for complete search history.

(56) References Cited

U.S. PATENT DOCUMENTS

| 5,609,878 | A * | 3/1997 | Gueyne et al. | 424/408 |
| 2003/0124165 | A1* | 7/2003 | Vollhardt et al. | 424/406 |
| 2006/0147562 | A1* | 7/2006 | Sommerville | 424/736 |
| 2006/0204468 | A1* | 9/2006 | Allef et al. | 424/70.13 |
| 2009/0069407 | A1* | 3/2009 | Gries et al. | 514/432 |

FOREIGN PATENT DOCUMENTS

| JP | 2002173407 | * | 6/2002 |
| WO | WO 2004/010783 A1 | * | 2/2004 |

* cited by examiner

*Primary Examiner* — Patricia Leith
(74) *Attorney, Agent, or Firm* — Thomas R. Vigil

(57) ABSTRACT

The insecticide comprises an insecticide particularly for killing bed bugs comprising nanospheres and primary ingredients of Organic Andirobia, Orange, Citronella, Organic Neem and Australian Myrtle oils. The insecticide can further comprise Isopropyl Alcohol as a carrier, Phenoxyethanol, Lavandox and *Leucojum Aestivum* Bulb Extract.

1 Claim, No Drawings

BED BUG INSECTICIDE

BACKGROUND OF THE INVENTION

1. Field of the Invention

The present invention relates to the formulation of an insecticide particularly adapted to kill bed bugs. The insecticide comprises nanospheres for slow release of the insecticide and primary ingredients of Organic Andirobia, Orange, Citronella, Organic Neem and Australian Myrtle oils.

2. Description of the Prior Art

Hertofore a variety of insecticides for killing bed bugs have been proposed. Two examples of previously proposed insecticide formulations using other active ingredients different from the ingredients disclosed herein are disclosed in U.S. Pat. Nos. 3,931,359 and 4,690,947. Also an insecticide using spherules for carrying the active ingredients of an insecticide are disclosed in U.S. Pat. Nos. 5,609,878 and 5,669,878.

BRIEF DESCRIPTION OF THE INVENTION

According to the present invention there is provided an insecticide particularly for killing bed bugs comprising nanospheres and primary ingredients of Organic Andirobia, Orange, Citronella, Organic Neem and Australian Myrtle oils. The insecticide can further comprise Isopropyl Alcohol, Phenoxyethanol, Lavandox and *Leucojum Aestivum* Bulb Extract.

DETAILED THE DESCRIPTION OF THE PREFERRED EMBODIMENTS OF THE INVENTION

The insecticide formulation of the present invention comprises primary and secondary ingredients and a special delivery system. This special delivery system is designed to penetrate the cuticle of the Bed Bug exoskeleton to deliver natural oils for Bed bug control. This delivery system is at the submicron particle size level (100-1000 nm), almost atomic. The Nanosphere is designed to slowly release its content when the sphere is in contact with a trigger factor such as the enzymes and water in the Insect's body. This also allows for a time release of the active ingredients over a long period of time. Examples of the nanospheres used are disclosed in U.S. Pat. No. 7,338,928

The active delivery system is initially dormant, until triggered by water or enzymes. This allows the natural oils comprising the active ingredients to also remain stable and effective, boosting efficacy. The oils used have been shown to not only repel, but kill the insect. Organic Andirobia, Orange, Citronella, Organic Neem and Australian Myrtle oils are the major components of the active ingredients carried by nanostructure. All of these oils traditionally have been used around the world for the control of many types of insects but not in the combination described herein or in the proportions or ranges described herein.

The formulation also contains Lavandox, which is a Mexican Lavender oily extract. This ingredient acts to numb (inhibits muscle contraction) of the insect.

Another secondary ingredient is IBR Snowflake which is a botanical extract containing an ingredient called Dormin. It acts on a cellular level to put the cells in a slowed dormant stage. By slowing down cellular division, it prevent the eggs of the bed bug (*Cimex lectularius*) from maturing at a normal rate.

Still another secondary ingredient is Phenoxyethanol which is not only a preservative, but also an anesthetic agent as well.

Further, the active ingredient's penetration is enhanced by alcohol as the carrier.

The percentages of the primary and secondary ingredients of the insecticide formulation are et forth below:

| Ingredient | % Range by weight |
| --- | --- |
| Isopropyl Alcohol | 5.0-99.9% |
| Andiroba Oil | 0.0001-5.00% |
| Orange Oil | 0.0001-5.000% |
| Neem Oil | 0.0001-5.000% |
| *Citronella* Oil | 0.0001-5.000% |
| Australian Myrtle Oil | 0.0001-5.000% |
| Nanosphere structure | 0.01%-30.000% |
| Phenoxyethanol | 0.1-2.0% |
| Lavandox | 0.1%-1.50% |
| *Leucojum Aestivum* Bulb Extract | 0.01-3.0% |

What is claimed is:

1. An insecticide in particular for killing bed bugs comprising:
   Isopropyl Alcohol in an amount of from 5.0-99.9% by weight,
   Andiroba Oil in an amount of from 0.0001-5.00% by weight,
   Orange Oil in an amount of from 0.0001-5.000% by weight,
   Neem Oil in an amount of from 0.0001-5.000% by weight,
   Citronella Oil in an amount of from 0.0001-5.000% by weight,
   Australian Myrtle Oil in an amount of from 0.0001-5.000% by weight,
   Nanosphere structures 0.01%-30.000% by weight,
   Phenoxyethanol in an amount of from 0.1-2.0% by weight,
   Lavandox in an amount of from 0.1%-1.50% by weight, and
   *Leucojum Aestivum* Bulb Extract in an amount of from 0.01-3.0% by weight, wherein each of said percentages are percentages by weight of the insecticide.

* * * * *